United States Patent [19]

Teed

[11] 4,309,236
[45] Jan. 5, 1982

[54] PROCESS FOR ATTACHING ELASTIC STRIPS DURING THE MANUFACTURE OF ELASTIC LEG DISPOSABLE DIAPERS

[75] Inventor: Richard K. Teed, Greenwood, S.C.

[73] Assignee: Riegel Textile Corporation, New York, N.Y.

[21] Appl. No.: 187,614

[22] Filed: Sep. 15, 1980

Related U.S. Application Data

[62] Division of Ser. No. 115,280, Feb. 8, 1980, Pat. No. 4,261,782.

[51] Int. Cl.³ .................. A61F 13/16; B32B 31/08
[52] U.S. Cl. .................................. 156/164; 156/229; 156/269; 156/302
[58] Field of Search ............... 156/164, 229, 361, 269, 156/265, 494, 519, 522, 302, 303; 226/119; 242/75, 753; 128/284 R, 287

[56] References Cited

U.S. PATENT DOCUMENTS

| | | | |
|---|---|---|---|
| 3,788,365 | 1/1974 | Campbell et al. | 2/237 |
| 3,828,367 | 4/1974 | Bourgeois | 156/164 |
| 3,867,940 | 2/1975 | Mesek et al. | 128/287 |
| 4,050,462 | 3/1976 | Wcon et al. | 128/287 |
| 4,081,301 | 3/1978 | Buell | 156/229 |
| 4,227,952 | 10/1980 | Sabee | 156/164 |
| 4,240,866 | 12/1980 | Rega | 156/519 |

Primary Examiner—Jerome W. Massie
Attorney, Agent, or Firm—Bell, Seltzer, Park and Gibson

[57] ABSTRACT

An apparatus and process for attaching elastic strips in elastic leg disposable diapers having gathered and extendible side portions in the crotch area during manufacture of such diapers in an assembly machine including mechanisms for alternately stretching and relaxing predetermined lengths of the elastic strips for adhesive attachment of the stretched lengths to the crotch area and the more relaxed lengths to the outer waist areas continuously along the edges of the diaper. These mechanisms include devices for feeding elastic strips at a predetermined constant rate for adhesive attachment in the diaper, nipping mechanisms engaging the elastic strips and defining a predetermined distance of travel of the elastic strips therebetween, movable devices for engaging the elastic strips and for alternately moving to other positions to vary the distance of travel of the elastic strips for alternately stretching and relaxing the elastic strips and compensating mechanisms for maintaining the stretching and the relaxing, respectively, during feeding of the stretched and relaxed lengths.

3 Claims, 15 Drawing Figures

PROCESS FOR ATTACHING ELASTIC STRIPS DURING THE MANUFACTURE OF ELASTIC LEG DISPOSABLE DIAPERS

CROSS REFERENCE TO RELATED APPLICATION

This is a division of earlier-filed co-pending application Ser. No. 115,280, filed Feb. 8, 1980, now U.S. Pat. No. 4,261,782.

FIELD OF THE INVENTION

This invention relates to an apparatus and more specific process for attaching elastic strips in elastic leg disposable diapers in accordance with the improved elastic leg disposable diaper and process for manufacturing same disclosed in co-pending U.S. patent application Ser. No. 7/085,372, filed Oct. 16, 1979, and assigned to the assignee of the present invention, wherein elastic strips are adhesively secured continuously along the longitudinal edges of the disposable diaper and are alternately secured in stretched condition along the crotch area and in a more relaxed condition along the outer waist areas to form gathered and extendible side portions in the crotch area for elastic conformance of such side portions with the legs of the wearer.

BACKGROUND OF THE INVENTION

The novel elastic leg diaper product and broad process of inserting elastic strips therein which are alternately stretched and relaxed and continuously secured along the longitudinal edges of the diapers to overcome problems resulting from prior art processes and to produce an improved diaper product are fully set forth in assignee's above-identified co-pending application and reference may be had thereto for a full discussion of same.

Additionally, an example of a suitable apparatus is disclosed in co-pending application Ser. No. 6/085,382, filed Oct. 16, 1979, now U.S. Pat. No. 4,239,578, and assigned to the assignee of the present application, for inserting elastic strips during the manufacture of elastic leg disposable diapers in accordance with the improved elastic leg disposable diaper and process for manufacturing same disclosed in the above-mentioned co-pending U.S. Patent application Ser. No. 6/085,372.

It is the object of this invention to provide a further apparatus (in addition to that disclosed in assignee's co-pending application Ser. No. 6/085,382) and a more specific process for attaching elastic strips in elastic leg disposable diapers having gathered and extendible side portions in the crotch area during the manufacture of such diapers in an assembly machine in accordance with the broad process and resulting elastic leg disposable diaper product of assignee's co-pending application Ser. No. 6/085,372.

SUMMARY OF THE INVENTION

By this invention, it has been found that the above object may be accomplished by providing an apparatus and process, generally as follows.

Means are provided for alternately stretching and relaxing predetermined lengths of the elastic strips for adhesive attachment of the stretched lengths to the crotch area and the more relaxed lengths to the outer waist areas continuously along the longitudinal edges of the diaper, wherein the means for alternately stretching and relaxing predetermined lengths of the elastic strips include the following:

Means feed continuous elastic strips at a predetermined constant rate from a supply into desired position in the diapers for adhesive attachment therein. Two spaced-apart nipping means cooperate with the feeding means and engage the elastic strips during feeding thereof and define a predetermined distance of travel of the elastic strips between the nipping means. One of the nipping means is positioned at the point of adhesive attachment of the elastic strips in the diapers. Movable means are positioned for engaging the elastic strips as they are fed between the nipping means and for alternately moving to other positions to vary the distance of travel of the elastic strips for alternately stretching and relaxing lengths of the elastic strips.

Inasmuch as the feeding of elastic strips necessarily places some tension and causes some stretching and cannot be accomplished in a totally tensionless or relaxed condition and since the elastic strips are being fed at a constant rate from the supply which must be less than the length of the diapers since portions thereof are being attached in stretched condition and since the elastic strips are in effect underfed for the relaxed lengths and overfed for the stretched lengths, some means must be provided for compensating for these conditions. Accordingly, means are connected with the elastic strip engaging means for moving same and for quickly increasing the distance of travel of the elastic strips for stretching lengths of the elastic strips and incrementally further increasing the distance of the travel of the elastic strips for a predetermined period of time to compensate and maintain the stretching of the lengths of the elastic strips while they are being fed into position in the diapers, and then quickly decreasing the distance of travel of the elastic strips for relaxing lengths of the elastic strips and incrementally further decreasing the distance of travel of the elastic strips for a predetermined period of time to compensate and maintain the relaxing of the lengths of elastic strips while they are being fed into position in the diapers.

Preferably, a timed control means is connected with the means for moving said elastic strip engaging means for operating such means in timed correlation with the speed of movement of the diapers through the assembly machine and the lengths of the longitudinal edges of the crotch area and the waist areas to which alternate lengths of stretched and relaxed portions of the elastic tapes are to be attached.

BRIEF DESCRIPTION OF THE DRAWINGS

Some of the objects and advantages of this invention having been set forth, other objects and advantages will appear when taken in conjunction with the accompanying drawings, in which.

DETAILED DESCRIPTION OF THE INVENTION

Figures 13, 14:
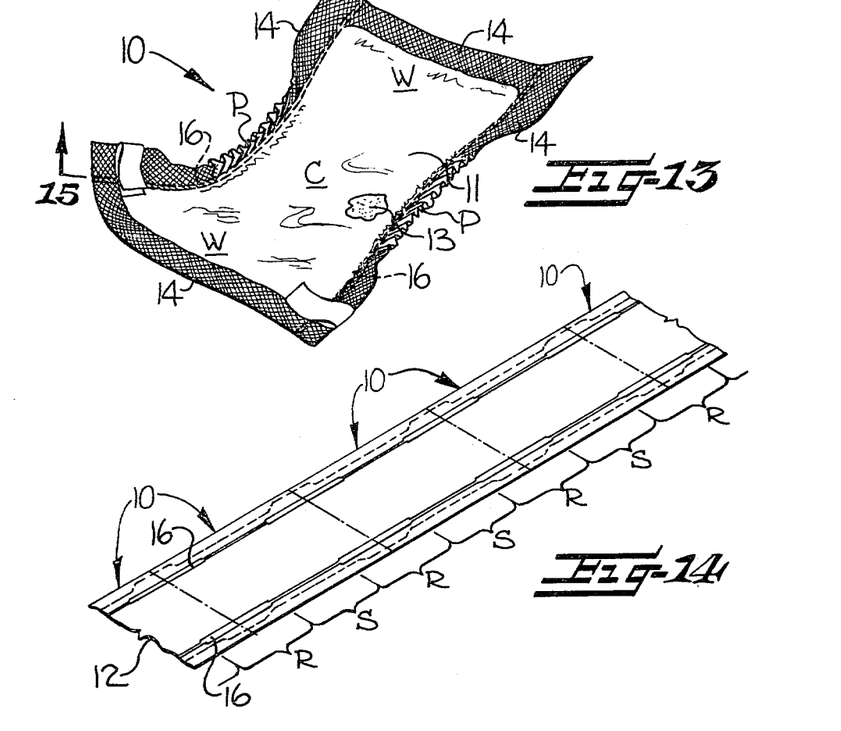
FIG. 13 is a top perspective view of an elastic leg disposable diaper produced by the apparatus and process of this invention and shown in generally relaxed condition.
FIG. 14 is a top perspective view of interconnected diapers produced by the apparatus of FIG. 1.
Figure 15:
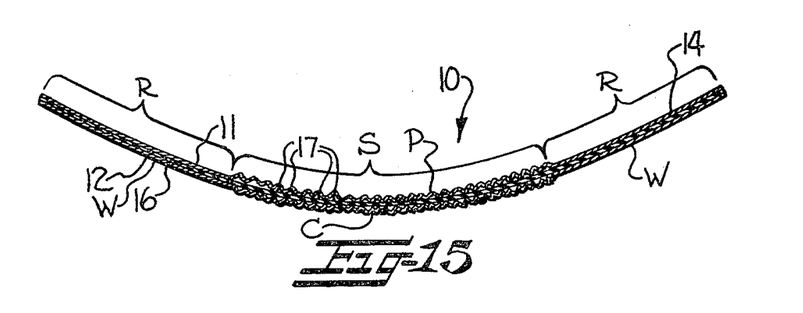
FIG. 15 is a sectional view through the diaper of FIG. 13 and taken generally along the line 15—15 of FIG. 13.

In the drawings, FIGS. 1–12 illustrate the apparatus and process of this invention for attaching elastic strips during the manufacture of elastic leg disposable diapers and FIGS. 13–15 illustrate the resulting elastic leg disposable diaper product.

Referring firstly to the elastic leg disposable diaper product produced by the apparatus of this invention for purposes of background, the improved elastic leg disposable diaper, as discussed more fully in the above-identified co-pending application Ser. No. 6/085,372 of the assignee of this invention, is referred to generally by the reference numeral 10. The diaper 10 is preferably of generally hourglass configuration and has a central crotch area C and outer waist areas W designed to be placed around and fit the crotch and waist of the wearer when the diaper 10 is placed on the wearer in conventional manner. The diaper 10 further includes a fluid-permeable top cover sheet 11, a fluid impermeable bottom cover sheet 12 and a fluid-absorbent interior pad 13, all of which may be of conventional construction.

The disposable diaper 10 is secured along its longitudinal and transverse edges by suitable adhesive or other attachment means 14 which secures the top cover sheet 11 and the bottom cover sheet 12 and generally provides an envelope around the interior pad 13 which is unsecured at its longitudinal edges and in the central crotch area C to either the top cover sheet or bottom cover sheet to allow the interior pad 13 to conform to the shape of the wearer when placed in position on the wearer.

The diaper 10 further includes elastic strips 16 extending and being secured by adhesive or other suitable means 17 to the diaper 10 continuously along the full length of the outside longitudinal edges of the diaper 10. The elastic strips 16 are secured in the crotch area C in stretched elastically-contractible condition forming gathered and extendible side portions P in the crotch area for elastic conformance with the legs of the wearer and are secured in the waist areas W in less elastically-contractible or relaxed condition so as to provide less or no gathering of the side portions of the waist areas W.

Figure 1:
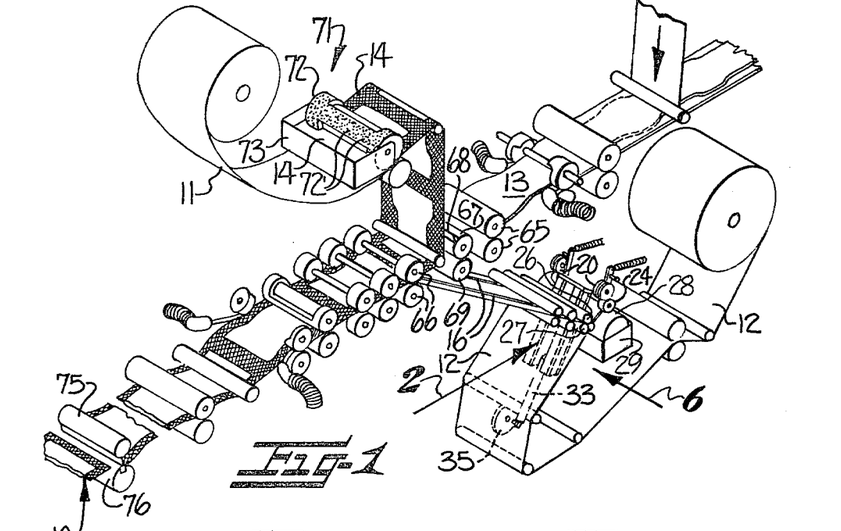
FIG. 1 is a schematic, perspective view of apparatus for manufacturing elastic leg diapers utilizing the improved apparatus of this invention.
Figure 2:
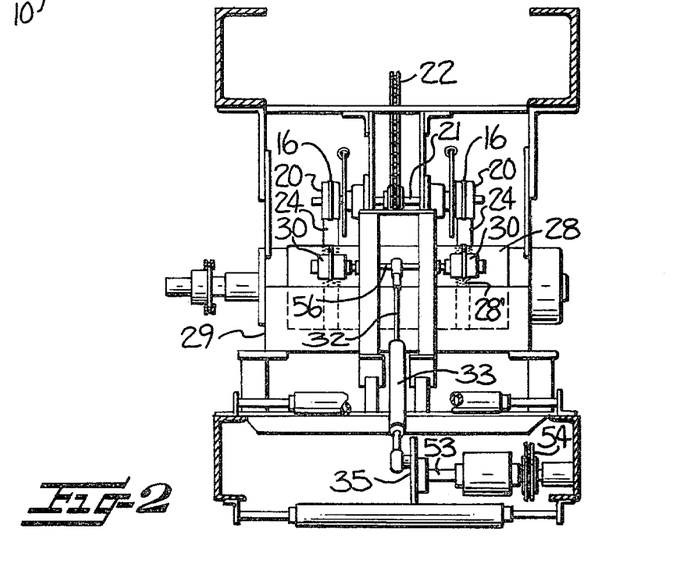
FIG. 2 is an elevational view, partly in section, of the apparatus of this invention and taken generally in the direction of arrow 2 in FIG. 1.

Referring now to the apparatus of the present invention, FIG. 1 illustrates schematically an apparatus for manufacturing elastic leg disposable diapers 10 utilizing the apparatus of this invention for attaching elastic strips 16 during the manufacture of such elastic leg disposable diapers 10. The apparatus of this invention is shown schematically therein and many of the drives of the overall diaper manufacturing apparatus are eliminated for purposes of clarity of the disclosure and such drives or other devices may be easily designed by those with ordinary skill in the art. However, details of construction and operation of apparatus for manufacturing disposable diapers may be seen in co-pending application Ser. No. 6/046,114, filed June 6, 1979, and prior U.S. Pat. No. Re. 28,139 and U.S. Pat. No. 3,984,272, all of which are assigned to the assignee of the present invention and which are applicable for use with the apparatus for attaching elastic strips of the present invention.

In FIG. 1, connected multi-layer interior absorbent pads 13 are shown being fed through spaced-apart pairs of driven feed rolls 65, 66 between which is provided a pad severing means in the form of a rotating cutting roll 67 having a knife blade 68 thereon and an anvil roll 69 which operate to intermittently cut the interconnected multi-layer interior pads 13 transversely for separation of the interconnected pads 13. The driven feed rolls 66 are driven somewhat faster than the driven feed rolls 65 to effect an overfeeding of the severed interior pads 13 for spacing of the interior pads 13 apart in the further fabrication of the disposable diapers 10.

Immediately prior to the feed rolls 66, the top cover sheet 11 is fed from a suitable source of supply to feed rolls 66 through a glue applicator 71 which applies the glue or adhesive 14 of a suitable type in a predetermined pattern across the top cover sheet 11 at spaced locations and along the longitudinal edges for purposes of gluing the transverse and longitudinal edges of the ultimately fabricated disposable diaper 10 together. Glue applicator 71 may comprise any suitable glue applicator for the above purpose and as illustrated herein may include a glue applicator roll 72 having indentations or cups 72' therein which collectively are of the predetermined configuration of the areas for receiving adhesive 14. The applicator roll 72 may pass through an adhesive supply tank 73 for containing a supply of the adhesive 14.

Simultaneously with the above, the bottom cover sheet 12 is fed from a source of supply to feed rolls 66 and into superimposed position under the spaced-apart interior pads 13 and top cover sheet 11 so that all of these components are in superimposed position. The top cover sheet 11 and bottom cover sheet 12 are pressed into contact with each other by the feed rolls 66 and subsequent rolls and are adhesively secured together along longitudinal edges and transversely between the separated and spaced-apart interior pads 13 to form serially-interconnected disposable diapers 10, as shown generally in FIGS. 1 and 14, which are continuously fed through the remaining portions of the apparatus of FIG. 1 by suitable feeding means.

These serially-interconnected diapers 10 are fed through a series of mechanisms, not shown, and are ultimately fed between cutter roll 75 and anvil roll 76 which cut the serially-interconnected diapers 10 transversely between interior pads 13 to form individual diapers 10.

Cooperating with the above-described apparatus for manufacturing disposable diapers 10, apparatus in accordance with this invention is provided for attaching elastic strips 16 during the manufacture of such disposable diapers 10. This apparatus includes means for alternately stretching and relaxing predetermined lengths of elastic strips for adhesive attachment of the stretched elastic lengths S to the crotch area C and the more relaxed lengths R to the outer waist areas W continuously along the longitudinal edges of the diaper, as may be seen particularly in FIGS. 14 and 15.

This apparatus comprises, firstly, means for feeding continuous elastic strips 16 from any suitable source of supply (not shown) at a predetermined constant rate into desired position for adhesive attachment in the diapers. As illustrated particularly in FIGS. 3 and 4, the feeding means may include driven feed rolls 20 commonly mounted on a driven shaft 21 for receiving the elastic strips 16 from a suitable source of supply (not shown). From the feed rolls 20, the elastic strips are fed into engagement with the bottom cover sheet 12 for immediate adhesive attachment thereto and are then fed by the feed rolls 66 into position with the remaining components of the disposable diapers 10, as shown in FIG. 1. The drive shaft 21 is driven by a suitable chain drive 22 from a shaft 23 which may, in turn, be driven by suitable drive mechanisms from the diaper fabricating machine (not shown) at a predetermined constant rate.

Figures 6, 7:
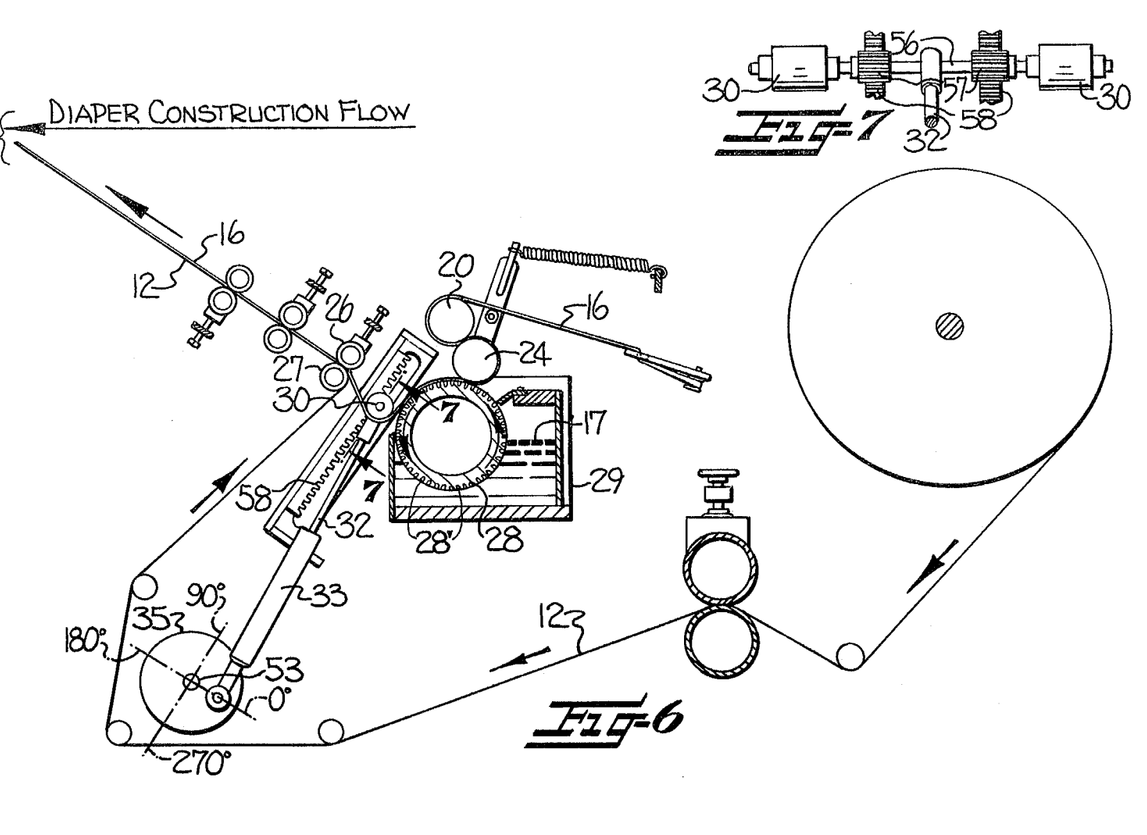
FIG. 6 is an enlarged, side elevational, schematic view of a portion of the apparatus of FIG. 1 and taken generally in the direction of the arrow 6 of FIG. 1.
FIG. 7 is a partial, elevational view, taken generally along the line 7—7 of FIG. 6.

The means for alternately stretching and relaxing predetermined lengths of the elastic strips 16 further includes two spaced-apart nipping means cooperating with the feeding means and engaging the elastic strips 16 during the feeding thereof and defining a predetermined distance of travel of the elastic strips 16 between the nipping means. In the embodiment of the apparatus illustrated herein, the two spaced-apart nipping means comprise the feeding rolls 20 and cooperating guide rolls 24 which are suitably mounted for pivotal biased engagement with the feed rolls 20, as shown in FIG. 6, and the elastic strips 16 pass in generally an S-shaped path around the feed rolls 20 and the guide rolls 24 and are nipped therebetween to form the first nipping means. The second nipping means consists of a pair of opposed rolls 26, 27 which are mounted for nipping engagement with each other in any suitable manner and are spaced from the first nipping means 20, 24 to form a predetermined distance of travel of the elastic strips therebetween, as may be seen in FIG. 6. This second nipping means 26, 27 also receives the bottom cover sheet 12 so that the elastic strips 16 are adhesively attached to this diaper component at this point.

From the nipping means formed by the rolls 20, 24 the elastic strips 16 pass over and into contact with a driven adhesive applicator roll 28 which includes cups or indentations 28' therein for picking up adhesive 17 as it passes through a supply tank 29 containing such adhesive 17. The applicator roll 28 is adapted to apply adhesive continuously along one of the faces of each of the elastic strips 16 as they are fed past the driven applicator roll 28. The driven applicator roll 28 may also be in nipping engagement with the guide rolls 24 and constitute the first nipping means. The adhesive 17 is desirably of a fast-acting type since the elastic strips are being secured in both the stretched and relaxed condition and the adhesive must set up as soon as the elastic strips are moved into contact with one of the components of the disposable diaper 10, such as the bottom cover sheet 12 in the case of the apparatus illustrated herein.

The means for alternately stretching and relaxing predetermined lengths of the elastic strips 16 further comprises movable means, such as rolls 30, positioned for engaging the elastic strips 16 as they are fed between the nipping means 20, 24 or 24, 48 and 26, 27 and for alternately moving to other positions (as shown in FIGS. 9-12) to vary the distance of travel of the elastic strips 16 between such nipping means for alternately stretching and relaxing lengths of the elastic strips 16.

Means are connected with the elastic strip engaging roll means 30 for moving same and comprise a piston and cylinder 32, 33 connected to the roll means 30 and mounted for alternate quick movement to and from a contracted position (dotted line position of FIG. 10 and solid line position of FIG. 11) and an extended position (solid line positions of FIGS. 9, 10 and 12) for alternately moving the elastic strip engaging roll means 30 quickly to a position for increasing the distance of travel of the elastic strips 16 between the nipping means for stretching the lengths S of elastic strips 16 and then quickly to a position decreasing the distance of travel of the elastic strips 16 for relaxing lengths R of the elastic strips 16.

Figure 10:
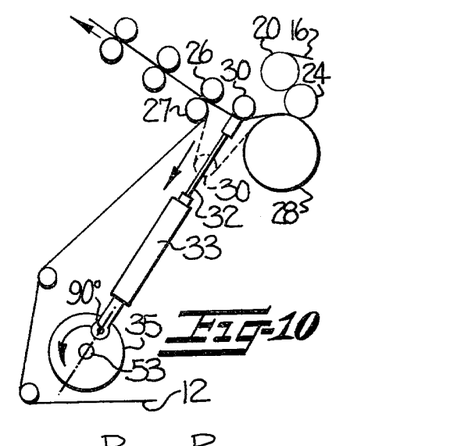
Figure 11:
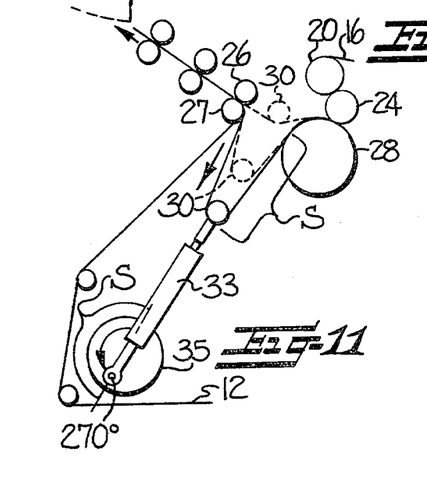
Figure 12:
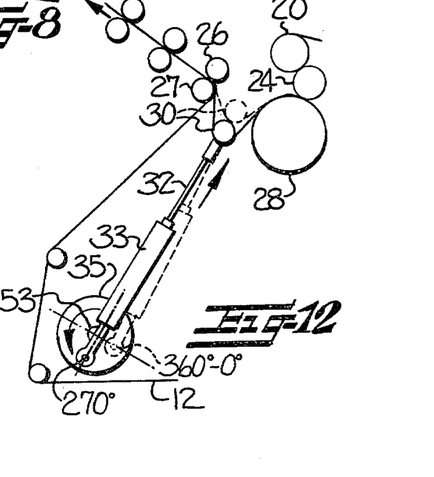

There is further provided a crank means including a rotating crank disc 35 and a crank arm which is formed by the piston and cylinder 32, 33 and has one end eccentrically pivotally mounted on the rotating crank disc and the other end carrying the elastic strip engaging roll means 30 for translating the rotary motion of the crank disc 35 to incremental reciprocation of the elastic strip engaging roll means 30 for alternately moving the elastic strip engaging roll means 30 to positions incrementally further increasing the distance of travel of the elastic strips 16 after the increase thereof by the piston and cylinder 32, 33 to maintain the stretching of the lengths S of elastic strips 16 during the feeding thereof (as is illustrated during rotation of the crank disc from the position of FIG. 10 to the position of FIG. 11) and then to positions incrementally further decreasing the distance of travel of the elastic strips 16 after the decrease thereof by the piston and cylinder means 32, 33 to maintain the relaxing of the lengths R of elastic strips 16 during the feeding thereof (as illustrated during the rotation of the crank disc 35 from the position shown in FIG. 11 to the position shown in FIG. 10).

Figures 3, 4, 5:
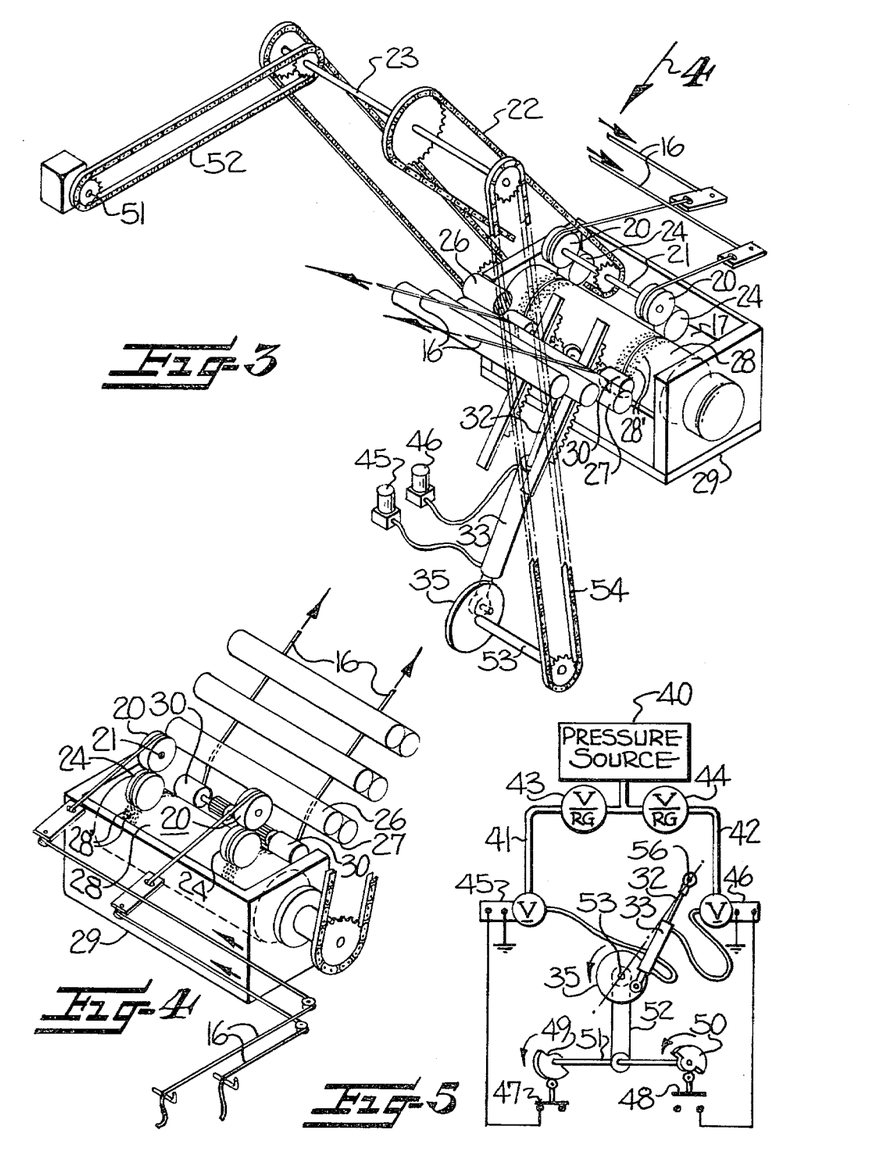
FIG. 3 is a schematic, perspective view of the apparatus of this invention with some devices omitted and with the bottom cover sheet of the diaper omitted for clarity of illustration.
FIG. 4 is a schematic, perspective view of the apparatus of this invention taken from the opposite side of the view of FIG. 3 and generally in the direction of the arrow 4 in FIG. 3 with some devices omitted and with the bottom cover sheet of the diaper omitted for clarity of illustration.
FIG. 5 is a schematic of the timed control means of the apparatus of this invention.

The means for alternately stretching and relaxing predetermined lengths of the elastic strips 16 further comprises timed control means (a schematic of which is illustrated in FIG. 5) connected with and controlling operation of the piston and cylinder 32, 33 and the crank means 35, 32 and 33, which form the means for moving the elastic strip engaging roll means 30, in correlation with the speed of movement of the diapers 10 through the assembly machine and the lengths of the longitudinal edges of the crotch area C and the waist areas W to which alternate stretched and relaxed lengths S, R of the elastic strips 16 are to be attached.

As shown in FIG. 5, this timed control means may comprise a source of pressurized air 40 which provides pressurized air to a pair of conduits 41, 42 through pressure regulating valves 43, 44 and to electrically operated valves 45, 46. From the valves 45, 46 the air conduits 41, 42 extend to opposite sides of the cylinder 33 for respective actuation of the piston and cylinder 32, 33 for quick movement to the extended position and the contracted position. The valves 45 and 46 are controlled for alternate actuation by electrical switches 47, 48 which are controlled by cams 49, 50 mounted on a common shaft 51 driven by a chain or belt drive 52 from a driven shaft 53 which carries and drives the crank disc 35. The shaft 53 is connected by chain or belt drive 54 to driven shaft 23 which is driven from drive mechanisms of the diaper assembly machine in timed correlation with the drives for feeding the diapers 10 through the assembly machine during their fabrication.

For stabilizing movement of the strip engaging rolls 30, they are mounted on a common shaft 56 attached to the piston 32 and which carries pinions 57 positioned for up and down movement in racks 58.

For operation of the above-described apparatus for attaching elastic strips 16 in elastic leg disposable diapers 10 during the manufacture of such diapers 10 in the assembly machine, the following operation and process may be utilized.

A typical disposable diaper 10 is approximately 17.8 inches in length and the central crotch area C would be approximately 8.9 inches in length and the outer waist areas 4.45 inches in length for a combined length of 8.9 inches. Therefore, in order to attach relaxed lengths R and stretched lengths S of the continuous elastic strips 16 alternately to the waist areas W and the crotch areas C of the interconnected diapers 10, as shown in FIG. 14, a relaxed length R of elastic strips 16 of approximately 8.9 inches must be fed by the apparatus of this invention into adhesive engagement in proper position along the longitudinal edges of the interconnected diapers 10 and then a stretched length S of the elastic strips 16 of approximately 8.9 inches must be fed into position in the diaper 10 which requires stretching of the stretched length S to approximately twice its original length which will result in the feeding of approximately 4.45 inches of unstretched elastic strips 16 for attachment in the crotch area C.

This stretching and relaxing is accomplished by actuation of the piston and cylinder mechanism 32, 33 from its extended position (FIG. 9) which feeds the elastic strips 16 in substantially relaxed condition into desired positions for attachment along abutting waist areas W of two interconnected diapers to the contracted position (dotted line position of FIG. 10) which doubles the length of travel of the elastic strips 16 between nipping means and stretches the elastic strips 16 so that the same effective length of elastic strips 16 are fed into position along the crotch area of the diaper 10, while only one-half that length or 4.45 inches of elastic strips are fed from the unstretched supply.

However, inasmuch as the elastic strips 16 are being fed at a constant rate from the supply, which can be no more than 4.45 inches for the stretched lengths S and 8.9 inches for the relaxed lengths R for a total of 13.35 inches of unstretched elastic strips per 17.8 inch diaper, and because the feeding of elastic strips necessarily places some tension and causes some stretching and cannot be accomplished in a totally tensionless or relaxed condition, some means must be provided for compensating for the tension or stretch caused by normal feeding and for the constant feeding rate which is in effect underfeeding for the relaxed lengths R and overfeeding for the stretched lengths S. This compensation is provided by the motion of the crank means which incrementally further increases the distance of travel of the elastic strips S for a predetermined period of time to maintain stretching of the lengths S of the elastic strips 16 after stretching thereof by the piston and cylinder 32, 33 and while they are being fed into position in the diapers 10 and then incrementally further decreases the distance of travel of the elastic strips 16 for a predetermined period of time after they have been relaxed by operation of the piston and cylinder 32, 33 to maintain the relaxing of the lengths R of elastic strips 16 while they are being fed into position in the diapers 10.

Figure 8:
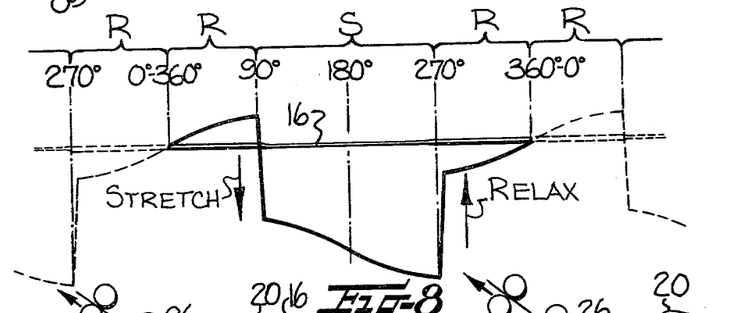
FIG. 8 is a diagram illustrating the motion of the devices of the apparatus of this invention.
Figure 9:
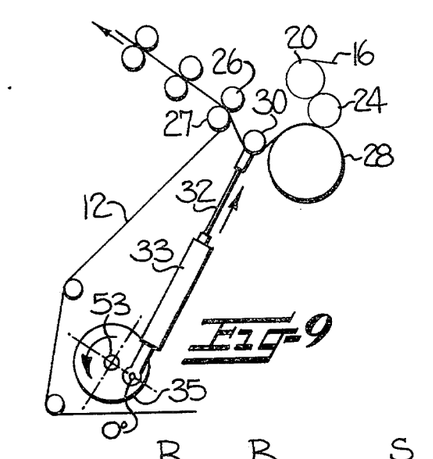
FIGS. 9–12 are side, elevational, schematic views illustrating a portion of the apparatus shown in FIG. 6 with the devices in various positions during operation of the apparatus of this invention.

Referring now to the diagram of FIG. 8 and FIGS. 9-12 which show relative positions of the piston and cylinder 32, 33 and the crank means 35 and 32, 33 during various positions of operation, it may be seen in FIG. 9 that when the crank means is in its 0° position which is the position in which the elastic strips 16 are being attached at the start of a waist area W of one of the interconnected diapers 10, the elastic strips 16 are in a relatively relaxed condition. To maintain this relaxed condition during the feeding of the strips 16, the crank mechanism rotates around to its 90° position of FIG. 10 which in effect incrementally decreases the distance of travel of the elastic strips 16 between nipping points to further relax the elastic strips 16 for the purposes discussed above and as indicated in the diagram of FIG. 8. At this position, the piston and cylinder mechanism is operated by the opening of valve 46 through the closing of switch 48 by cam 50 to move the piston and cylinder 32, 33 to its contracted position as shown in dotted lines in FIG. 10. This immediately doubles the length of the path of travel of the elastic strips 16 between nipping points for stretching the lengths S of elastic strips 16. This stretch is maintained for a predetermined period of time during rotation of the crank disc 35 to its 270° position as shown in FIG. 11 during which the predetermined distance of travel of the elastic strips 16 is incrementally further increased by effective downward movement of the roll 30 to the position shown in FIG. 11 and as indicated in the diagram of FIG. 8. At this point, the piston and cylinder mechanism 32, 33 is operated by the opening of valve 45 by the switch 47 being closed by cam 49 to move the piston and cylinder 32, 33 to its extended position, as indicated in dotted lines in FIG. 11 and in solid lines in FIG. 12, for quickly relaxing the elastic strips 16 as indicated in the diagram of FIG. 8. This relaxing is maintained during the next 90° of rotation of the cam disc 35 by incrementally further decreasing the predetermined distance of travel of the elastic strips 16 between nipping points, as indicated in the diagram of FIG. 8, through the moving of the roll 30 upward as indicated in dotted lines in FIG. 12. The cycle of operation of alternately stretching and relaxing the elastic strips 16 for application to one disposable diaper 10 has now been completed and the cycle is repeated.

As will be readily understood by those with ordinary skill in the art, it is difficult if not impossible to obtain complete relaxation of the elastic strips 16 during any feeding operation and the term "relaxed" as used herein and as results from a practical operation of the apparatus of this invention and the practice of the process herein is relative and is intended to cover the feeding and application of elastic strips 16 in a "more relaxed" condition when compared to the stretched condition. Accordingly, the elastic strips 16 will probably always be somewhat or slightly tensioned or stretched even in the waist areas W of the disposable diaper 10.

Accordingly, the present invention has provided a process of securing elastic strips 16 within longitudinal edges of elastic leg disposable diapers 10 having a central crotch area C and outer waist areas W to form gathered and extendible side portions P in the crotch area C of the diapers 10 during manufacture of such diapers after severing of the interconnected diapers and allowing the stretched lengths S of the elastic strips 16 in the waist areas W to contract.

The process of this invention comprises generally the steps of feeding continuous elastic strips 16 at a predetermined constant rate from a supply into desired position in contact with the longitudinal edges of the diapers 10, while effecting adhesive securement therebetween along the entire length of the edges. Predetermined lengths of the continuous elastic strips 16 are alternately stretched and relaxed during the feeding step for securing the stretched lengths S of the continuous elastic strips 16 to the crotch area C and the relaxed lengths R of the continuous elastic strips 16 to the waist areas W of the diapers. This step comprises nipping the elastic strips 16 during the feeding thereof at spaced-apart points to define a predetermined distance of travel of the elastic strips 16 between the nipping points, quickly increasing the distance of travel of the elastic strips 16 for stretching lengths S of the elastic strips 16 and incrementally further increasing the distance of travel of the elastic strips 16 for a predetermined time period to maintain the stretching of the lengths S of the elastic strips 16 while they are being fed into position in the diapers 10 and then quickly decreasing the distance of travel of the elastic strips S for relaxing lengths R of the elastic strips 16 and incrementally further decreasing the distance of travel of the elastic strips 16 for a predetermined period of time to maintain the relaxing of the lengths R of the elastic strips 16 while they are being fed into position in the disposable diapers. Preferably, adhesive is applied continuously to the elastic strips during the feeding step along the entire length of the elastic strips 16.

In the drawings and specification, there has been set forth a preferred embodiment of the invention and although specific terms are employed, they are used in a generic and descriptive sense only and not for purposes of limitation.

What is claimed is:

1. A process of securing elastic strips within longitudinal edges of elastic leg disposable diapers having a central crotch area and outer waist areas to form gathered and extendible side portions in the crotch area of the diapers during manufacture of such diapers; said process comprising the steps of:
    feeding continuous elastic strips at a predetermined constant rate from a supply into desired position within the longitudinal edges of the diapers, while effecting adhesive securement therebetween along the entire length of the edges; and
    alternately stretching and relaxing predetermined lengths of the continuous elastic strips during said feeding step, while securing the stretched lengths of the continuous elastic strips to the crotch area and the relaxed lengths of the continuous elastic strips to the waist areas of the diapers, comprising nipping the elastic strips during the feeding thereof at spaced-apart points to define a predetermined distance of travel of the elastic strips between the nipping points, quickly increasing the distance of travel of the elastic strips for stretching lengths of the elastic strips and incrementally further increasing the distance of travel of the elastic strips for a predetermined period of time to maintain the stretching of the lengths of the elastic strips while they are being fed into position in the diapers, and then quickly decreasing the distance of travel of the elastic strips for relaxing lengths of the elastic strips and incrementally further decreasing the distance of travel of the elastic strips for a predetermined period of time to maintain the relaxing of the lengths of elastic strips while they are being fed into position in the diapers.

2. A process, as set forth in claim 1, further including the step of
    applying adhesive continuously to the elastic strips during said feeding step along the entire length of the elastic strips.

3. A process for manufacturing elastic leg disposable diapers having a central crotch area, outer waist areas and elastic extendible side portions in the crotch area, said process comprising the steps of:
    superimposing a continuous fluid-permeable top cover sheet, a continuous fluid-impermeable bottom cover sheet and spaced-apart fluid-absorbent interior pads;
    securing the top cover sheet and bottom cover sheet together along longitudinal edges and transversely between the interior pads to form serially-interconnected disposable diapers;
    securing elastic strips continuously along the entire length of the longitudinal edges of each of the diapers including feeding continuous elastic strips at a predetermined constant rate from a supply into desired position in contact with the longitudinal edges of the diapers, while effecting adhesive securement therebetween along the entire length of the edges, and alternately stretching and relaxing predetermined lengths of the continuous elastic strips during said feeding step, while securing the stretched lengths of the continuous elastic strips to the crotch area and the relaxed lengths of the continuous elastic strips to the waist areas of the diapers, comprising nipping the elastic strips during the feeding thereof at spaced-apart points to define a predetermined distance of travel of the elastic strips between the nipping points, quickly increasing the distance of travel of the elastic strips for stretching lengths of the elastic strips and incrementally further increasing the distance of travel of the elastic strips for a predetermined period of time to maintain the stretching of the lengths of the elastic strips while they are being fed into position in the diaper, and then quickly decreasing the distance of travel of the elastic strips for relaxing lengths of the elastic strips and incrementally further decreasing the distance of travel of the elastic strips for a predetermined period of time to maintain the relaxing of the lengths of elastic strips while they are being fed into position in the diapers; and
    cutting the interconnected diapers transversely between interior pads to form individual diapers;
    whereby, the stretched lengths of the elastic strips will contract and form gathered and extendible side portions in the crotch areas of the individual diapers.

* * * * *